US009194793B2

(12) United States Patent
Adachi et al.

(10) Patent No.: US 9,194,793 B2
(45) Date of Patent: Nov. 24, 2015

(54) SAMPLE ANALYSIS DEVICE (75) Inventors: Sakuichiro Adachi, Kawasaki (JP);
Kunio Harada, Hachioji (JP); Isao Yamazaki, Ryugasaki (JP); Masaharu Kiyama, Higashimatsuyama (JP);
Takeshi Fujita, Niiza (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 351 days.

(21) Appl. No.: 13/002,664

(22) PCT Filed: Jul. 30, 2009

(86) PCT No.: PCT/JP2009/063573
§ 371 (c)(1),
(2), (4) Date: Jan. 5, 2011

(87) PCT Pub. No.: WO2010/013777
PCT Pub. Date: Feb. 4, 2010

(65) Prior Publication Data
US 2011/0110822 A1 May 12, 2011

(30) Foreign Application Priority Data
Jul. 30, 2008 (JP) ................... 2008-196337

(51) Int. Cl.
*G01N 21/59* (2006.01)
*G01N 21/25* (2006.01)
*G01N 35/02* (2006.01)
*G01N 21/03* (2006.01)
*G01N 35/00* (2006.01)
*G01N 35/04* (2006.01)

(52) U.S. Cl.
CPC ............ *G01N 21/253* (2013.01); *G01N 35/025* (2013.01); *G01N 21/0332* (2013.01); *G01N 21/255* (2013.01); *G01N 2035/00386* (2013.01); *G01N 2035/0455* (2013.01); *G01N 2201/0231* (2013.01); *G01N 2201/0415* (2013.01); *G01N 2201/0453* (2013.01); *G01N 2201/0624* (2013.01); *G01N 2201/0627* (2013.01)

(58) Field of Classification Search
CPC ..................................................... G01N 21/255
See application file for complete search history.

(56) References Cited

U.S. PATENT DOCUMENTS 4,141,954 A * 2/1979 Shigetomi ........................ 422/64
4,234,538 A * 11/1980 Ginsberg et al. ................. 422/64
(Continued)

FOREIGN PATENT DOCUMENTS

EP       1 153 752 A2    11/2001
JP       57-020646       2/1982
(Continued)

OTHER PUBLICATIONS

Extended European Search Report issued in European Patent Application No. 09803019.0 on Jun. 26, 2014.

*Primary Examiner* — P. Kathryn Wright
(74) *Attorney, Agent, or Firm* — Baker Botts L.L.P.

(57) ABSTRACT

Using an LED element as a light source, a photometric unit including the light source, a light receiving element and other components therebetween is reduced in size. A holder 30 detachable from the device as a unit holds a light emission unit 15 formed of an LED and a light receiving element 21, and the holder is placed inside a thermostatic chamber 18 which holds a constant temperature fluid 17. Thus, the photometric unit is reduced in size.

15 Claims, 7 Drawing Sheets

(56) References Cited

U.S. PATENT DOCUMENTS

| | | | |
|---|---|---|---|
| 4,451,433 A | | 5/1984 | Yamashita et al. |
| 4,762,413 A | * | 8/1988 | Namba et al. ............ 356/339 |
| 4,940,332 A | | 7/1990 | Miwa et al. |
| 5,645,800 A | * | 7/1997 | Masterson et al. ............ 422/65 |

FOREIGN PATENT DOCUMENTS

| | | | |
|---|---|---|---|
| JP | 57-142346 | | 9/1982 |
| JP | 63-055464 | | 3/1988 |
| JP | 04-027846 | | 1/1992 |
| JP | 11-174059 | | 7/1999 |
| JP | 2001-208760 | | 8/2001 |
| JP | 2002-5818 | | 1/2002 |
| JP | 2003-279585 | * | 10/2003 |
| JP | 3964291 | | 6/2007 |
| JP | 2007-198935 | | 8/2007 |
| JP | 2007-218633 | | 8/2007 |
| JP | 2007-256033 | | 10/2007 |
| JP | 2008-014638 | | 1/2008 |

* cited by examiner

SAMPLE ANALYSIS DEVICE

TECHNICAL FIELD

The present invention relates to an analysis device for analyzing the amounts of ingredients included in a sample, and relates to an automatic analyzing device for analyzing the amounts of ingredients included in blood or urine, for example.

BACKGROUND ART

As an analysis device for analyzing the amounts of ingredients included in a sample, widely used is an automatic analyzing device in which light from a light source is radiated on a sample or a reaction solution which is a mixture of a sample and a reagent, the amount of transmitted light of each of one or multiple measurement wavelengths having passed through the sample or the reaction solution is measured in a light receiving element to calculate a light absorbance, and the amount of ingredients is determined from a relationship between the light absorbance and concentration (see Patent Document 1, for example). The automatic analyzing device needs multiple measurement wavelengths to handle a large number of test items, and needs to be capable of stably measuring a certain amount of light or more for each of all the wavelengths to achieve highly accurate measurement. Conventionally, a halogen lamp or the like which emits a relatively large amount of light and which has a broad emission spectrum has been used as a light source. As this light source, application of a light emitting diode (LED) which is a semiconductor light emitting element has been considered in recent years. An LED is advantageous in that it is low cost, has long life and can contribute to size reduction. To secure a certain amount of light, however, a conventional method is designed in which: an LED is placed outside a thermostatic chamber that keeps the temperature of a reaction solution constant; and light from the LED is converged through an optical system using optical components such as lenses, and then is radiated to cells in the thermostatic chamber and to a light receiving element (see Patent Document 2, for example). For this reason, a photometric unit including the light source and the light receiving element is large, and therefore is not necessarily reduced in size. In addition, an LED element which is a light emitting part of the LED has disadvantages in that the light amount and emission spectrum vary due to self-heating and variation in the environmental temperature. Although as a means for discharging heat, there has been so far proposed a configuration in which heat is discharged by an aluminum block (see Patent Document 3, for example), the reduction in size is limited since a certain capacity is required near the light source to discharge heat by use of a solid block.

PRIOR ART DOCUMENT

Patent Document

Patent Document 1: U.S. Pat. No. 4,451,433
Patent Document 2: JP 2007-218633 A
Patent Document 3: JP Patent No. 3964291

DISCLOSURE OF THE INVENTION

Problems to be Solved by the Invention

Since a conventional automatic analyzing device using an LED as a light source requires an optical system for converging light to ensure a certain light amount and a temperature control mechanism, the use of the LED does not always lead to size reduction of the photometric unit which includes the light source, the light receiving element and other components therebetween.

Particularly, an automatic analyzing device requires 0.01% stability in the light amount and 0.1 nm or lower stability in the emission spectrum to ensure inspection accuracy. In the conventional method, self-heating of the LED varies the temperature of the element, and thereby varies the light amount and emission spectrum, so that measurement cannot be performed stably. As a typical example, in an LED, a 1° C. variation in the temperature of the element causes a 0.1% variation in the light amount. Hence, to stably keep the variation in the light amount to 0.01% or lower, the variation in the temperature of the element needs to be restricted to 0.1° C. or lower. Moreover, an LED element is known to have a property in which a 1° C. variation in the temperature of the element causes approximately a 0.1 nm variation in the central wavelength of emitted light, and thus the emission spectrum varies. Although it is possible to periodically detect the degree of the aforementioned variation in the light amount by using water as a reaction solution, the variation in the emission spectrum cannot be detected in the light receiving element since the light is not dispersed. Accordingly, the temperature variation in the LED element needs to be surely kept at 0.1° C. or lower. However, a specific method for achieving the above has not been disclosed.

In addition, variation in the light amount is attributable not only to the temperature of the LED element but also to a light path of the optical system. A variation in the temperature of the entire optical system causes a holder of holding the LED element and the optical receiver to expand or shrink, which varies the light path length that is a distance between the LED element and the optical receiver. This varies the light amount.

Such temperature variation in the LED element and variation in the light path vary the light amount. If the variation in the light amount is large, measurement cannot be performed accurately. Accordingly, for a more accurate measurement, the temperature of the element needs to be kept constant and the temperature of the entire optical system also needs to be kept constant.

Means for Solving the Problems

A holder holding an LED element and a light receiving element is placed in a thermostatic chamber which holds a constant temperature fluid. The holder is typically configured as a unit including a first vertical arm having the light emission unit embedded therein, a second vertical arm having the light receiving element embedded therein, and a connection arm connecting lower parts of the first vertical arm and the second vertical arm. Surfaces, which face each other, of the first vertical arm and the second vertical arm are preferably flat surfaces, and side surfaces next to the surfaces are preferably curved surfaces. The light emission unit includes a light emitting diode and a heat discharge plate for discharging heat generated by the light emitting diode to the constant temperature fluid in the thermostatic chamber. In addition, the holder may be detachable. In an automatic analyzing device, the constant temperature fluid inside the thermostatic chamber is always controlled accurately within 37° C.±0.1° C. to keep the temperature of the reaction solution constant. The light emission unit as well as a distance between the light emission unit and the light receiving unit can be kept constant by immersing the holder in the constant temperature fluid inside the thermostatic chamber.

Effects of the Invention

According to the present invention, the photometric unit can be reduced in size by placing the holder, in which the light source and light receiving element are integrated, inside the thermostatic chamber holding the constant temperature fluid. Moreover, by providing flat surfaces facing each other on inner sides of the holder, the light source and light receiving element can be provided closer to the cell holding the reaction solution, so that the components can be arranged compactly. By thus arranging the components compactly, the distance between the light source and light receiving element is shortened, so that it becomes easy to ensure light of a certain amount or more. In addition, since the temperature of the holder can be controlled with the constant temperature fluid, variation in the light path due to temperature variation in the LED element and light receiving element is suppressed, the light amount and emission spectrum are kept stable for a long period of time, whereby measurement can be performed with high accuracy by keeping a stable emission spectrum while maintaining 0.01% stability in the light amount.

MODES FOR CARRYING OUT THE INVENTION

Hereinafter, an embodiment of the present invention will be described with reference to the drawings.

First Example

Figure 1:
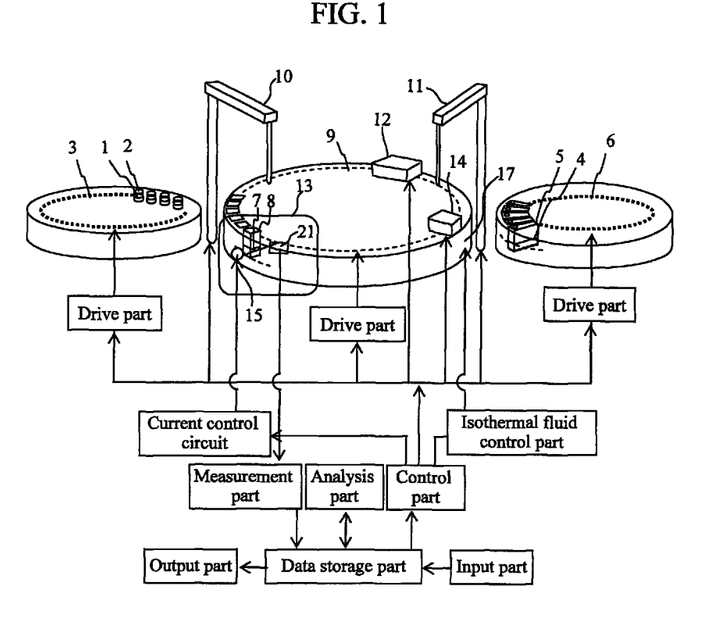
FIG. 1 is a schematic view showing an overall configuration example of an analysis device.

FIG. 1 is a schematic view showing an overall configuration example of an analysis device according to the present invention. Multiple sample cups 2 containing samples 1 are arranged in a sample disk 3. Multiple reagent bottles 5 containing reagents 4 are arranged in a reagent disk 6. Multiple cells 8 are arranged in a cell disk 9, each of the cells 8 containing a reaction solution 7 obtained by mixing the sample 1 and the reagent 4 therein. A sample pipetting mechanism 10 moves a certain amount of the sample 1 from the sample cup 2 to the cell 8. A reagent pipetting mechanism 11 moves a certain amount of the reagent 4 from the reagent bottle 5 to the cell 8. A stir unit 12 stirs and mixes the sample 1 and the reagent 4 inside the cell 8. A measurement unit 13 includes a light emission unit 15 which is a light source for radiating light to the reaction solution 7 and a light receiving element 21 for receiving light having passed the reaction solution 7. The cell 8 having finished the analysis is cleaned by a cleaning unit 14, and into this cell, the next sample is pipetted by the sample pipetting mechanism 10 as well as a new reagent is pipetted by the reagent pipetting mechanism 11. The cell 8 is immersed in a constant temperature fluid 17 held in a thermostatic chamber 18, so that the cell 8 and the reaction solution 7 contained therein are moved while temperatures thereof are kept constant.

The analysis device further includes: a current control circuit for supplying a certain current to the light emission unit; a control part for controlling respective units of the device; drive parts for rotationally driving the sample disk, the reagent disk, and the cell disk separately according to instructions from the control part; a constant temperature fluid control part for controlling the temperature and flow rate of the constant temperature fluid; a data storage part for storing various data; an input part for inputting necessary data from the outside to the data storage part; a measurement part for calculating a light absorbance from the amount of light received by the light receiving element 21; an analysis part for determining the amount of ingredients from light absorbance data; and an output part capable of displaying data and outputting the data to the outside.

The amount of a certain ingredient in the sample 1 is analyzed through the following procedure. Firstly, a certain amount of the sample 1 in the sample cup 2 is pipetted by the sample pipetting mechanism 10 into the cell 8. Next, a certain amount of the reagent 4 in the reagent bottle 5 is pipetted by the reagent pipetting mechanism 11 into the cell 8. During these pipetting operations, the sample disk 3, the reagent disk 6, and the cell disk 9 are rotationally driven by the respective drive parts under control of the control part, so that the sample cup 2, the reagent bottle 5, and the cell 8 are moved to predetermined positions within reach of the pipetting mechanisms. Subsequently, the sample 1 and the reagent 4 in the cell 8 are stirred by the stir unit 12 to obtain the reaction solution 7. The light absorbance of the reaction solution 7 is measured every time the cell 8 passes the measurement unit 13 during rotation of the cell disk 9, and light absorbance data is sequentially accumulated in the data storage part. Normally, the inside of the cell 8 is cleaned by the cleaning mechanism 14 after performing photometry for about ten minutes, and then the next analysis is performed. At this time, if necessary, another reagent 4 is additionally pipetted by the reagent pipetting mechanism 11 into the cell 8 after the elapse of a certain time period and stirring is performed by the stir unit 12. The cell 8 is further subjected to measurement for a certain time period, and thus light absorbance data of the reaction solution 7 after the elapse of the certain time period is stored in the data storage part. The accumulated light absorbance data is subjected to analysis by the analysis part to analyze the amount of ingredients on the basis of calibration curve data of each test item. Data required for control or analysis by each unit is inputted from the input part to the data storage part. Various data and analysis results are displayed and outputted by the output part.

Figure 2:
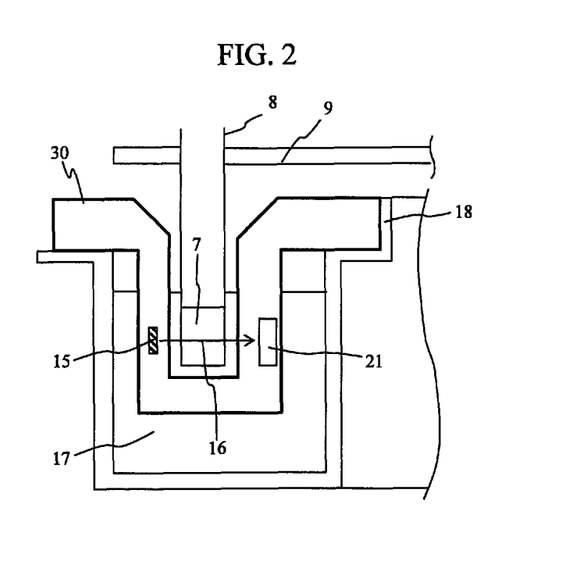
FIG. 2 is a schematic cross sectional view showing a configuration example of a measurement unit.

FIG. 2 is a schematic cross sectional view showing a configuration example of the measurement unit 13. Inside the thermostatic chamber 18, the constant temperature fluid 17 whose temperature and flow rate are controlled by the control part is brought in and circulated, so that the cell 8 holding the reaction solution 7 and arranged in the cell disk 9 is immersed in the constant temperature fluid 17. Water was used as the constant temperature fluid 17 and the temperature thereof was controlled to 37±0.1° C. which is a reaction temperature. The light emission unit 15 and the light receiving element 21 are integrally held by a detachable holder 30. An LED element was used as the light emission unit 15.

Figure 3:
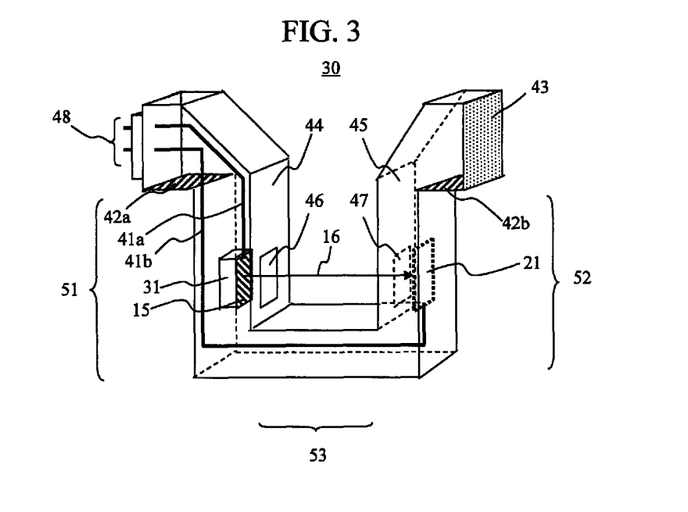
FIG. 3 is a perspective view showing a configuration example of a holder.

FIG. 3 is a perspective view showing a configuration example of the holder 30. The holder 30 includes a first vertical arm 51 having the light emission unit 15 embedded therein, a second vertical arm 52 having the light receiving element 21 embedded therein, and a connection arm 53 connecting and unifying lower parts of the first and second vertical arms 51 and 52. The first vertical arm 51 and the second vertical arm 52 have an exit surface 44 and an entrance surface 45 facing each other on inner sides thereof, respectively. A light exit window 46 and a light entrance window 47 are provided on the exit surface 44 and the entrance surface 45, respectively. The light emission unit 15 receives supply of a current from the current control unit through a wiring 41a and emits light 16. Light 16 is emitted from the light exit window 46 into the constant temperature fluid 17. As shown in FIG. 2, the light having passed the reaction solution 7 inside the cell 8 which is positioned between the exit surface 44 and the entrance surface 45 enters the holder 30 from the light entrance window 47, and is received by the light receiving element 21. The received light is transmitted through a wiring 41b as an electrical signal to the measurement part and is measured as light absorbance data. A heat discharge plate 31 is held on the back surface of the light emission unit 15.

Figure 4A:
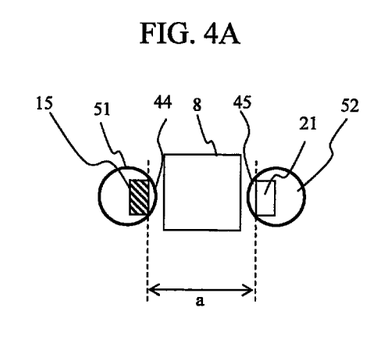
FIGS. 4A to 4C are schematic cross sectional views each showing an exit surface and an entrance surface as seen from above.
Figure 4B:
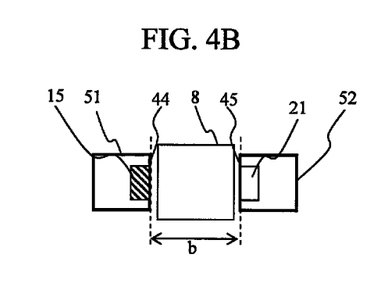
Figure 4C:
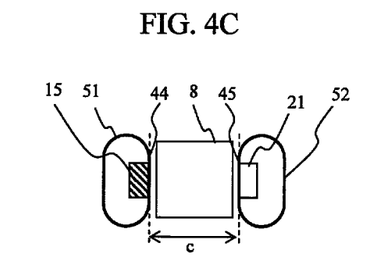

FIGS. 4A to 4C are schematic cross sectional views each showing the exit surface 44 and the entrance surface 45 as seen from above. Disturbance of the flow of the constant temperature fluid 17 by the placement of the holder in the constant temperature fluid 17 causes bubbles, fungus or contamination which makes it difficult to perform the analysis. Hence, it is important to form the holder in a shape that disturbs the flow of the constant temperature fluid 17 as little as possible. If the exit surface 44 and the entrance surface 45 of the holder are curved surfaces as in FIG. 4A, it is advantageous since the holder can be placed without disturbing the flow of the circulating constant temperature fluid 17. However, a distance a between the light emission unit 15 and the light reception element 21 is long, which is disadvantageous from the viewpoint of reduction in the system size. If the exit surface 44 and the entrance surface 45 are flat surfaces as in FIG. 4B, a distance b between the light emission unit 15 and the light receiving element 21 is shorter and the photometric unit can be further reduced in size. Moreover, as shown in FIG. 4C, if the exit surface 44 and the entrance surface 45 are flat surfaces while side surfaces next to the exit surface 44 and the entrance surface 45, that is, the surface on the side from which the circulating constant temperature fluid flows in and the surface on the side to which the constant temperature fluid flows out are curved surfaces, the photometric unit can be reduced in size without disturbing the flow of the constant temperature fluid.

Figure 5A:
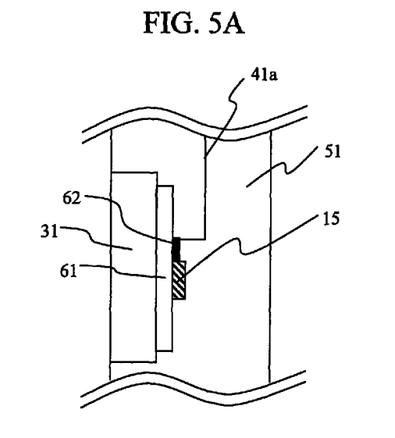
FIGS. 5A and 5B are diagrams each showing a configuration example of a heat discharge plate.
Figure 5B:
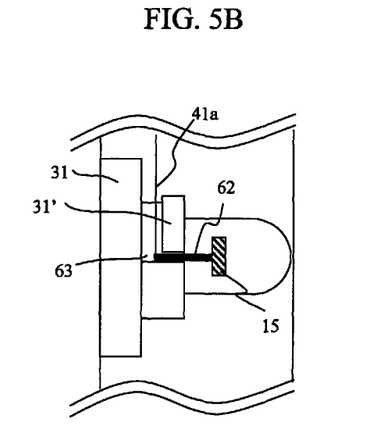

FIGS. 5A and 5B each show a configuration example of the heat discharge plate on the back surface of the light emission unit. There are two main types of commercially available LEDs which are flat type LEDs and round type LEDs. To keep the temperature of the LED element constant, it is important to control the temperature of the lead frame which is directly connected with the LED element. In the case of a flat type LED, the leadframe is wired on a plane and heat can be discharged easily by controlling the temperature of a flat plate on the back surface of the LED element. An example of this type of LED element is LUXEON STAR of Philips Lumileds Lighting Company. FIG. 5A shows a configuration for discharging heat of a flat type LED. Here, a flat plate 61 in contact with a leadframe 62 which is directly connected with the LED element being the light emission unit 15 is arranged so as to come into contact with the heat discharge plate 31. Silicone grease for temperature control is applied between the flat plate 61 and the heat discharge plate 31 for smooth transfer of the temperature. The leadframe 62 is connected to the wiring 41a and a current is supplied thereto. FIG. 5B shows a configuration for discharging heat of a round type LED. The leadframe 62 is wrapped with a thermally conductive insulation sheet 63, contacted with a heat discharge plate 31', and the temperature thereof is controlled by the external constant temperature fluid 17 through the heat discharge plate 31. An a GEL sheet of TAICA Corporation was used as the thermally conductive insulation sheet. With this configuration, the amount of light emitted from the LED element can be kept constant.

As the material of the holder 30, that is, a material which is water-proof so that the constant temperature fluid 17 does not enter the holder 30, and which blocks light so that light does not enter the light receiving element 21 inside the holder 30, BMC (bulk molding compound) was used in this example. The material of the light exit window 46 and the light entrance window 47 was a clear material such as glass, cyclic olefin polymer, or polystyrene, and the windows were sealed so that the constant temperature fluid 17 does not flow into the holder 30. By providing the holder 30 with the exit surface and entrance surface which do not allow fluid to pass through but allow light to pass through, measurement can be easily performed in the constant temperature fluid. Although water has been used as the constant temperature fluid 17 in this example, air, silicone oil, or fluorinated oil may be used instead. In the case where the constant temperature fluid 17 is silicone oil or fluorinated oil, the material of the holder 30 needs to be resin or material which is not eroded by oil, such as polystyrene or metal.

In addition, accuracy of the position of the holder 30 relative to the moving cell 8 is extremely important for determining the accuracy of the measurement, and if the position accuracy is low, the reaction solution inside the cell may not be measured in some cases. In this example, as shown in FIG. 3, the holder 30 is provided with horizontal fixation surfaces 42a and 42b as well as a vertical fixation surface 43 which are fixation parts, and thus can be attached to the thermostatic chamber 18 with high position accuracy. In addition, wirings for supplying power and receiving signals are required between the holder 30 and the device. However, attachment of the holder to the device becomes complicated if the wirings are drawn directly from the inside of the holder and connected to the device. The holder 30 of this example includes an electrode socket 48 connected to the wirings 41a and 41b, and thus power supply from the outside and signal output from the inside can be inputted and outputted easily.

Although water has been used as the constant temperature fluid in this example, the same effects can be obtained by using air or oil.

Figure 6:
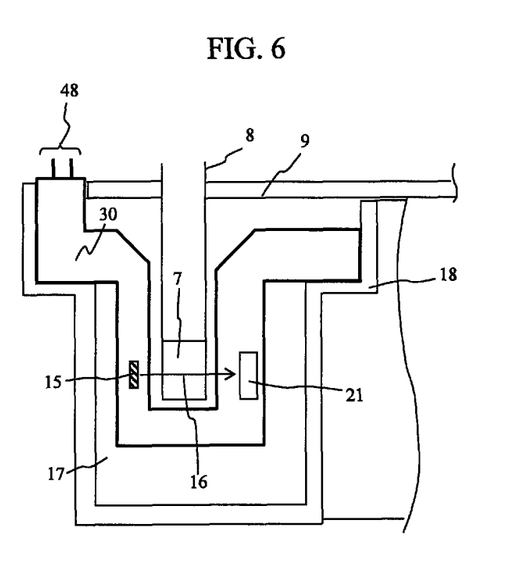
FIG. 6 is a diagram showing a configuration example of a measurement unit in the case of using air as a constant temperature fluid.

FIG. 6 shows a configuration example of the measurement unit in the case of using air as the constant temperature fluid. In the case where the constant temperature fluid is air, the thermostatic chamber 18 and the cell 8 are arranged so that the gap therebetween is made small. With this configuration, only a small amount of air from the outside of the thermostatic chamber is mixed with the constant temperature fluid, and a preferable temperature control capability can be maintained.

In addition, a lens made of clear material such as glass, cyclic olefin polymer, or epoxy resin, or a slit or the like made of light-blocking material that does not allow light to pass through may be provided inside the holder 30 to form an optical system for converging light emitted from the light emission unit.

According to this example, at least a part of the holder 30, which holds the light emission unit 15 and the light receiving element 21 and which is detachable from the device as a unit, is placed inside the thermostatic chamber 18 in such a manner that the measured light path passes through the constant temperature fluid. With this configuration, a certain amount of light is ensured while achieving reduction in the device size. In addition, by placing the holder 30 inside the thermostatic chamber, position variation due to the variation in the temperatures of the light source and the light receiving element is suppressed, which enables a highly accurate measurement with a small variation in the light amount.

Second Example

An automatic analyzing device is required to measure various test items at the same time. However, wavelengths to be used in the measurements vary depending on the test items and on the reagents. For example, 340 nm and 405 nm for UN (urease) (L-type Wako UN of Wako Pure Chemical Industries, Ltd.), 405 nm and 505 nm for ALP (Alkaline Phosphatase) (L-type Wako ALP•J of Wako Pure Chemical Industries, Ltd.), 600 nm and 800 nm for CRP (C-reactive protein) (LT auto Wako CRP of Wako Pure Chemical Industries, Ltd.), and the like. In this example, a configuration example is shown in which multiple light emission units 15 are provided in an integrated manner in a single holder so that multiple test items can be measured simultaneously. The entire configuration of the analysis device and other conditions not described below are the same as the first example.

Figure 7:
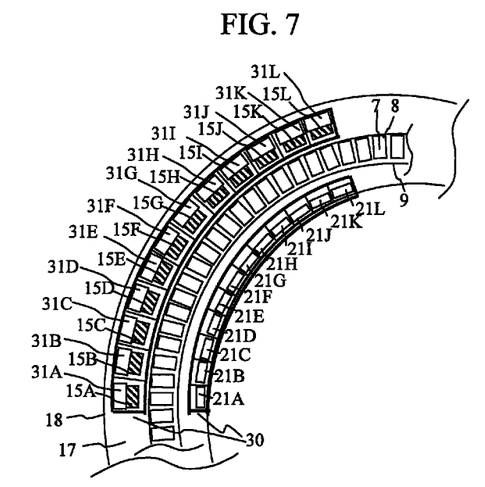
FIG. 7 is a diagram showing a configuration example of the measurement unit.

FIG. 7 shows a configuration example of a measurement unit 13 of this example. A holder 30 includes twelve types of light emission units 15A to 15L and light receiving elements 21A to 21L corresponding to the types of measurement wavelengths. The holder 30 is formed in an arc shape so that the multiple light emission units and light receiving elements are arranged with cells 8 interposed therebetween, the cells 8 arranged in a cell disk 9 and moving along a circular orbit. LED elements emitting measurement wavelengths of 340 nm, 405 nm, 450 nm, 480 nm, 505 nm, 546 nm, 570 nm, 600 nm, 660 nm, 700 nm, 750 nm, and 800 nm were used as the light emission units 15A to 15L, respectively. Thus, by arranging multiple LED elements having different emission wavelengths, measurement wavelengths of multiple test items can be selected and analyzed simultaneously.

The light emission units 15A to 15L are in contact with heat discharge plates 31A to 31L, and heat from self-heating of the light emission units 15A to 15L can be discharged to a constant temperature fluid 17 through the heat discharge plates 31A to 31L. In addition, a partition is provided between each pair of adjacent light emission units 15A to 15L and between each pair of adjacent light receiving elements 21A to 21L, to prevent light from light emission units other than the light emission unit facing each light receiving element from entering the light receiving element. According to this example, the multiple light emission units 15 and light receiving elements 21 are provided and the wavelength of light emitted from the light emission unit 15 is varied, whereby light absorbance data of multiple wavelengths can be measured in a compact device configuration.

Third Example

In this example, shown is a configuration example of a case where multiple holders are arranged on the same circumference. The entire configuration of the analysis device and other conditions not described below are the same as the first example.

Figure 8:
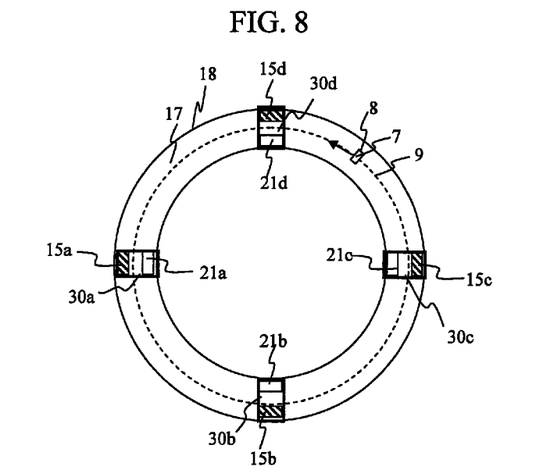
FIG. 8 is a diagram showing a configuration example of the measurement unit.

FIG. 8 is a diagram showing a configuration example of the measurement unit 13 according to this example. Multiple holders are arranged on the same circumference so that light emission units and light receiving elements are arranged with a cell 8 interposed therebetween, the cell 8 placed in a cell disk 9 and moving along a circular orbit. By thus configuring the photometric unit as a holder placed in a thermostatic chamber with a light emission unit and a light receiving element held therein, multiple photometric units can be arranged easily. In the example of FIG. 8, four holders 30a to 30d are arranged at angular positions of 0°, 90°, 180°, and 270° relative to the center of the cell disk 9, respectively. Light emission units 15a to 15d of the holders 30a to 30d emit light of the same wavelengths.

Measurement is performed whenever the cell 8 placed in the cell disk 9 and rotating in an anticlockwise direction passes any of the holders 30a to 30d. Four times the amount of data acquired with a single holder can be acquired within the same time period by arranging, on the same circumference, the four holders 30a to 30d including the light emission units 15a to 15d which emit light having the same wavelengths. Thus, measurement can be performed with high accuracy by increasing the temporal resolution of light absorbance data of a reaction solution 7.

Fourth Example

In this example, shown is a configuration example of a case where cells are arranged in a multiplexed manner in a cell disk 9 to achieve a higher throughput of the analysis device. While most parts of the entire configuration of the analysis device is the same as the first example, this example is different in that cells 8 are arranged on multiple concentric circles in the cell disk 9.

Figure 9A:
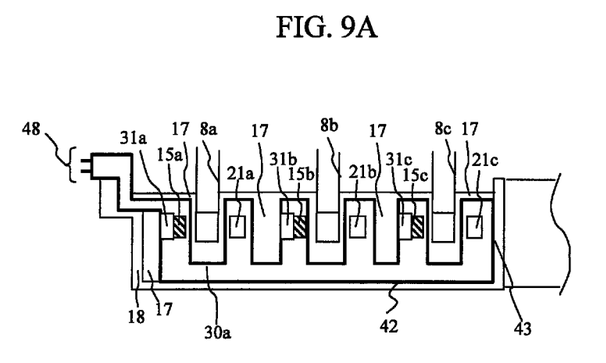
FIGS. 9A and 9B are diagrams each showing a configuration example of the measurement unit.
Figure 9B:
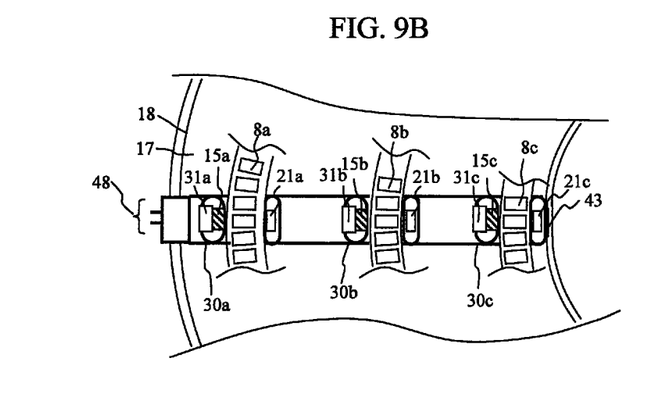

FIGS. 9A and 9B are diagrams each showing a configuration example of the measurement unit 13 according to this example. FIG. 9A is a schematic cross sectional view of the measurement unit, and FIG. 9B is a schematic top view thereof. In the example of FIGS. 9A and 9B, holders 30 holding light emission units 15a to 15c and light receiving elements 21a to 21c are arranged for samples 7a to 7c provided inside the cells 8a to 8c which are respectively held on three concentric circles formed on different radius positions of the cell disk. Each pair of the light emission unit and light receiving element is embedded in a pair of vertical arms, and bottom edges of the vertical arms are integrally connected by a connection arm. All of wirings in the holder 30 can be collectively connected to the outside by an electrode socket 48, Heat from self-heating of LED elements used as the light emission units 15a to 15c can be discharged to a constant temperature fluid through heat discharge plates 31a to 31c. According to this example, measurement can be performed with a higher throughput by arranging the cells on multiple circumferences having different radii and arranging, on each of the multiple circumferences, at least one holder 30 which is detachable from the device as a unit.

DESCRIPTION OF SYMBOLS 1 sample
2 sample cup
3 sample disk
4 reagent 5 reagent bottle
6 reagent disk
7 reaction solution
7a to 7c reaction solution
8 cell
8a to 8c cell
9 cell disk
10 sample pipetting mechanism
11 reagent pipetting mechanism
12 stir unit
13 measurement unit
14 cleaning unit
15 light emission unit
15A to 15L light emission unit
15a to 15d light emission unit
16 light
17 constant temperature fluid
18 thermostatic chamber
21 light receiving element
21A to 21L light receiving element
21a to 21d light receiving element
30 holder
30a to 30d holder
31 heat discharge plate
31' heat discharge plate
31A to 31L heat discharge plate
31a to 31c heat discharge plate
41a and 41b wirings
42 horizontal fixation surface
42a and 42b horizontal fixation surface
43 vertical fixation surface
44 exit surface
45 entrance surface
46 light exit window
47 light entrance window
48 electrode socket
51 first vertical arm
52 second vertical arm
53 connection arm
61 flat plate
62 leadframe
63 thermally conductive insulation sheet

The invention claimed is:

1. A sample analysis device comprising:
a thermostatic chamber which holds a liquid;
a controller which controls the temperatures of the liquid so that the liquid comprises a constant temperature liquid which is held in the thermostatic chamber;
a plurality of cells which contain a reaction solution;
a cell disk which holds the plurality of cells being immersed in the constant temperature liquid inside the thermostatic chamber;
a drive part which rotationally drives the cell disk; and
a holder which holds a light emission unit for generating light to be radiated to the cell and a light receiving element for detecting the light having passed through the cell, characterized in that the holder is immersed in the constant temperature liquid and placed inside the thermostatic chamber,
wherein the light emission unit and the light receiving element are integrally built into a part of the holder that is immersed in the constant temperature liquid, and
wherein the holder includes a first vertical arm having a flat first surface and a second vertical arm having a flat second surface, the first and second surfaces facing each other with the cell containing the reaction solution positioned therebetween, and
wherein the flat first surface adjoins a first side surface of the first vertical arm and the flat second surface adjoins a second side surface of the second vertical arm, the first and second side surfaces being curved surfaces.

2. The sample analysis device according to claim 1 wherein the first vertical arm has the light emission unit embedded therein, the second vertical arm has the light receiving element embedded therein,
and the holder includes a connection arm which connects lower parts of the first vertical arm and the second vertical arm.

3. The sample analysis device according to claim 2, wherein the first arm includes a light exit window and the second arm includes a light entrance window.

4. The sample analysis device according to claim 2, wherein the cell disk holds cells at a plurality of different radius positions, and the holder includes a plurality of pairs of the first vertical arm and the second vertical arm corresponding to the plurality of radius positions.

5. The sample analysis device according to claim 1, wherein the light emission unit includes a light emitting diode and a heat discharge plate for discharging heat generated by the light emitting diode to the constant temperature liquid.

6. The sample analysis device according to claim 1, wherein the holder is detachable.

7. The sample analysis device according to claim 1, wherein a wall surface of the holder does not allow liquid to pass through and has a light blocking property.

8. The sample analysis device according to claim 1,
wherein the holder includes electrodes for inputting and outputting power and information from and to outside.

9. The sample analysis device according to claim 1, wherein the holder includes a fixation part for attaching the holder to the thermostatic chamber with high position accuracy.

10. The sample analysis device according to claim 1, wherein the holder includes a plurality of light emission units and a plurality of light receiving elements.

11. The sample analysis device according to claim 1, wherein a plurality of the holders are arranged in different positions of the thermostatic chamber.

12. The sample analysis device according to claim 10, wherein the plurality of light emission units include at least one of light emission units respectively having emission wavelengths of 340 nm, 405 nm, 450 nm, 480 nm, 505 nm, 546 nm, 570 nm, 600 nm, 660 nm, 700 nm, 750 nm, and 800 nm.

13. The sample analysis device according to claim 1, wherein the controller is configured to control a flow rate of the constant temperature liquid to circulate the constant temperature liquid in the thermostatic chamber.

14. The sample analysis device according to claim 13, wherein the controller is configured to control the temperature of the constant temperature liquid in the thermostatic chamber to be 37° C.±0.1° C.

15. The sample analysis device according to claim 1, wherein the controller is configured to control the temperature of the constant temperature liquid in the thermostatic chamber to be 37° C.±0.1° C.

* * * * *